United States Patent [19]

Hoeks

[11] Patent Number: 5,213,973
[45] Date of Patent: * May 25, 1993

[54] MICROBIOLOGICAL PROCESS FOR OXIDATION OF METHYL GROUPS

[75] Inventor: Frans Hoeks, Naters, Switzerland

[73] Assignee: Lonza Ltd., Basel, Switzerland

[ * ] Notice: The portion of the term of this patent subsequent to Apr. 14, 2009 has been disclaimed.

[21] Appl. No.: 725,478

[22] Filed: Jul. 3, 1991

[30] Foreign Application Priority Data

Jun. 6, 1990 [CH] Switzerland .......................... 2272/90
Oct. 1, 1990 [CH] Switzerland .......................... 3149/90

[51] Int. Cl.$^5$ ...................... C12P 17/00; C12P 17/10; C12P 17/06; C12R 1/40
[52] U.S. Cl. .................................... 435/117; 435/118; 435/119; 435/120; 435/121; 435/122; 435/123; 435/124; 435/125; 435/126; 435/253.3; 435/877
[58] Field of Search ............... 435/117, 118, 119, 120, 435/121, 122, 123, 124, 125, 126, 253.3, 877

[56] References Cited

U.S. PATENT DOCUMENTS

| | | | |
|---|---|---|---|
| 3,383,289 | 5/1968 | Raymond | 195/28 |
| 4,266,034 | 5/1981 | Patel et al. | 435/252.1 |
| 4,269,940 | 5/1981 | Patel et al. | 435/148 |
| 4,375,515 | 3/1983 | Patel et al. | 435/189 |
| 4,859,592 | 8/1989 | Hagedorn | 435/122 |
| 5,104,798 | 4/1992 | Kiener | 435/117 |

FOREIGN PATENT DOCUMENTS

| | | | |
|---|---|---|---|
| 0315949 | 5/1989 | European Pat. Off. | 435/877 |
| 1-120292 | 5/1989 | Japan | 435/877 |
| 228688 | 2/1969 | U.S.S.R. | |
| 302341 | 7/1971 | U.S.S.R. | |
| 417468 | 11/1974 | U.S.S.R. | |

OTHER PUBLICATIONS

Roempps Chemie-Lexikon, vol. 8, No. 5, (1987) p. 3411.
Harayama et al., J. Bacteriol. 171, (1989), pp. 5048-5055.
Burlage et al., Appln. Environ. Microbiol., 55, (1989), pp. 1323-1328.
Kulla et al., Arch. Microbiol., 135, (1983), pp. 1-7.
Abril, M. A., et al., J. Bacteriol., vol. 171, (1989), pp. 6782-6789.
The Prokaryotes, Ed. by Starr, M. P., et al. Springer Verlag, (1981), pp. 670-679.
J. von Eysmondt and Wandrey, Chem. Ing. Tech., vol. 62, No. 2 (1990) pp. 134 and 135.
Raymond, R. L., *Process Biochem.*, (1969), pp. 71-74.
Hosler and Eltz, *Fermentation Advances*, "Microbiol. Conversion of p-Xylene In Stirred Permenters", pp. 789-805.

*Primary Examiner*—Herbert J. Lilling
*Attorney, Agent, or Firm*—Fisher, Christen & Sabol

[57] ABSTRACT

A microbiological process for oxidation of methyl groups in aromatic 5- or 6-ring heterocycles to the corresponding carboxylic acid. The reaction of the heterocycle takes place by microorganisms of the genus Pseudomonas, which utilize toluene, xylene or cymene. An inducer, the aromatic heterocycle, as the substrate, and a carbon source and energy source are fed in and, after the maximal product concentration is reached, the product is separated.

19 Claims, No Drawings

MICROBIOLOGICAL PROCESS FOR OXIDATION OF METHYL GROUPS

BACKGROUND OF THE INVENTION

1. Field Of The Invention

The invention relates to a microbiological process for the oxidation of methyl groups on aromatic 5- or 6-ring heterocycles to the corresponding carboxylic acid, with the heterocycle exhibiting no substituent on the carbon atom adjacent to the methyl group to be oxidized.

2. Background Art

These carboxylic acid derivatives can be used, for example, as intermediate products for other chemical syntheses. For example, 2-pyrazinecarboxylic acid is an important intermediate product for the production of the tuberculostatic pyrazinamide (2-pyrazinecarboxylic acid amide) [*Roemps Chemie Lexikon*, vol. 8, No. 5, (1987), p. 3411].

Thorough studies on the microbiological production of carboxylic acids up to now were conducted with aromatic hydrocarbons. The production of carboxylic acids by microbiological oxidation of methylated aromatic compounds was described in detail in the works of Raymond et al. [Raymond et al., Process Biochem., (1969), pages 71 to 74]. U.S. Pat. No. 3,383,289 describes a process for the biochemical oxidation of methyl groups in aromatic hydrocarbons with a gram-positive microorganism strain of the genus Nocardia. Disadvantages of these processes include, for example, in the methyl group oxidation of aromatic hydrocarbons, the benzene ring of the corresponding acid being cleaved.

In regards to *Pseudomonas putida* ATCC 33015 it is known that the biochemical oxidation of the methyl groups are toluene to benzoic acid taking place in three steps. By the action of the toluene monoxygenase, benzyl alcohol first results which then in two other steps, that is, catalyzed by an alcohol dehydrogenase and an aldehyde dehydrogenase, is converted to the acid.

In this strain both the Xyl genes, which code for enzymes of the xylene decomposition, and the genes, which are responsible for the regulation of the Xyl genes, are on the plasmid pWWO. This archetypical Tol plasmid has already been thoroughly investigated in a molecular biological manner [Harayama et al., J. Bacteriol., 171, (1989), pages 5048 to 5055; Burlage et al., Appl. Environ. Microbiol. 55, (1989), pages 1323 to 1328].

Also microbiological processes for the oxidation of methyl groups of an N-heterocycle are known from the literature. According to Soviet Union Patent No. 417,468, 2-methylpyridine is oxidized with a gram-positive microorganism strain of the genus Nocardia to the corresponding acid.

Soviet Union Patent No. 228,688 describes a microbiological process for the production of nicotinic acid from 3-methylpyridine with a gram-positive microorganism of the genus Mycobacterium. A microbiological process for the production of nicotinic acid with gram-positive bacteria of the genus Nocardia is known from Soviet Union Patent No. 302,341.

The disadvantages of methyl group oxidation of N-heterocycles with gram-positive bacteria are that with these alkane-utilizing bacteria the mixture ratio of the alkane to the substance to be oxidized has to be precisely adjusted to achieve a biotransformation, and that no biotransformation of the substance takes place in the absence of the alkane, i.e., the alkane used for the induction always has to be present even in the reaction of the substrate. By comparison tests with the gram-positive bacterium Nocardia and gram-negative *Pseudomonas putida* ATCC 330of applicant, it was possible to show clearly that Nocardia even in the presence of an alkane, such as, dodecane, does not oxidize 3-methylpyridine to the corresponding nicotinic acid.

Further, U.S. Pat. No. 4,859,592 describes a process for the production of picolinic acid with Pseudomonas putida, an alkyl-substituted aromatic hydrocarbon being formed in the presence of molecular oxygen in a first step by a dioxygenase. The resultant 2-hydroxymuconic acid semialdehyde then being reacted in a second step with ammonia or a primary amine to the corresponding nicotinic acid. The disadvantage of this process is that the corresponding picolinic acid is formed only in the second step by the reaction of the 2-hydroxymuconic acid semialdehyde with ammonia.

A microbiological process for the oxidation of methyl groups on heterocycles is also described in commonly-owned U.S. Ser. No. 650,589, filed on Feb. 5, 1991, now U.S. Pat. No. 5,104,798, issued on Apr. 14, 1992, (Swiss Patent Application No. 458/90, filed on Feb. 13, 1990), (both of which are not prior art). In this process, the Pseudomonas microorganisms are cultured first in a culture medium, for example, with p-xylene as the sole carbon source and energy source, are afterward separated and then the biotransformation is performed by the addition of the feedstock. By exhaustion of the biomass activity, relative small product concentrations are achieved in this two-step process.

BROAD DESCRIPTION OF THE INVENTION

The main object of the invention is to avoid the disadvantages of the above-identified processes and to provide a process that can be performed on a large scale with high space-time yields, in which a much higher product concentration is achieved and the carboxylic acids are obtained in high yield after isolation. Other objects and advantages of the invention are set out herein or are obvious herefrom to one skilled in the art.

The objects and advantages of the invention are achieved by the microbiological process of the invention.

In the microbiological process, according to the invention, for the oxidation of at least one methyl group on aromatic 5- or 6-ring heterocycles, the heterocycle exhibiting no substituent on the carbon atom adjacent to the methyl group to be oxidized to the corresponding carboxylic acid, there are fed into a culture medium, containing microorganisms of the genus Pseudomonas which utilize toluene, xylene or cymene:

(i) an inducer,
(ii) the methylated aromatic 5- or 6-ring heterocycle as substrate for the biotransformation, and optionally
(iii) one or more carbon sources and energy sources.
After the maximal product concentration is achieved, the carboxylic acid is separated.

The reaction can be performed according to the invention with microorganisms of the genus Pseudomonas which utilizes toluene, xylene or cymene, preferably the species *Pseudomonas putida*, especially with microorganisms of the strain *Pseudomonas putida*, which utilizes xylene, deposited at the American Type Culture Collection, 12301 Parklawn Drive, Rockville, Md. 20852, U.S.A., under number ATCC 33015.

Also suitable for the process are mutants of these microorganisms as well as other microorganisms, into which the Tol plasmid, necessary for the reaction, has been introduced either by conjugation or by genetic engineering methods.

DETAILED DESCRIPTION OF THE INVENTION

In the invention process, preferably:

(a) the microorganisms are cultivated with the inducer until enough cells for the production are present;

(b) then feeding of the inducer is stopped;

(c) then the methylated aromatic 5- or 6-ring heterocycle and the carbon source and energy source are added until the microorganisms exhibit a decrease of activity for the biotransformation;

(d) then the activity of the microorganisms is regenerated by the feeding of the inducer, optionally by simultaneous stopping feeding of the carbon source and energy source; and (e) process steps (b) to (d) are repeated so that the biotransformation can be performed over prolonged periods and, thus, the maximal product concentration and/or continuous production process is performed and high space-time yields are achieved.

The process according to the invention for oxidation of methyl groups in aromatic 5- or 6-ring heterocycles is suitably performed so that in the first process step (a) according to the above-described preferred embodiment biomass, capable of production, is produced in a so-called batch phase. For this purpose, microorganisms in a known way are cultivated according commonly-owned U.S. Ser. No. 650,589, filed on Feb. 5, 1991 now U.S. Pat. No. 5,104,798, issued on Apr. 14, 1992, (or Swiss Patent Application No. 458/90, filed on Feb. 13, 1990) either with representatives of the compound series of toluene, xylene and its isomers or cymene and its isomers, such as, p-xylene, m-xylene, p-cymene, or with m-cymene as the inducer and sole carbon source and energy source in a mineral medium, such as, disclosed in Kulla et al., Arch. Microbiol. 135, (1983), pages 1 to 7, or they are cultivated with representatives of the compound series of toluene, xylene and its isomers or cymene and its isomers, such as, p-xylene, m-xylene, p-cymene, or with m-cymene, as the inducer in a complex medium, such as, "Nutrient Broth No. 2," Oxoid Ltd., England, or in a mineral medium, such as, disclosed in Kulla et al., Arch. Microbiol., 135, (1983), pages 1 to 7, with carbon sources, such as, carbohydrates, sugar alcohols, low-boiling aliphatic alcohols, aliphatic fatty acids or amino acids, as the carbon source and energy source.

The pertinent parts, including the drawings, of commonly-owned U.S. Ser. No. 650,859, filed on Feb. 5, 1991, now U.S. Pat. No. 5,104,798, issued on Apr. 14, 1992, and entitled "Microbiological Oxidation Of Methyl Groups In Heterocycles", are incorporated herein. U.S. Ser. No. 650,859 discloses details of the cultivation of Pseudomonas microorganisms.

As substrates for the reaction methylated aromatic 5-member ring heterocycles can suitably be used, which contain one or more heteroatoms from the series of oxygen, nitrogen and sulfur, such as, methylated thiophenes, methylated furans, methylated pyrroles, methylated thiazoles, methylated pyrazoles or methylated imidazoles, which exhibit no substituent on the carbon atom adjacent to the methyl group to be oxidized. Preferably methylated furans, methylated thiophenes, methylated pyrroles and methylated thiazoles are used. 3,5-dimethylpyrazole, 5-methylthiazole, 4-methylthiazole, 2,5-dimethylthiophene, 2-methylthiophene, 3-methylthiophene, 2,5-dimethylfuran and 2,5-dimethylpyrrole are especially used as 5-member ring heterocycles.

The reaction can be suitably performed with aromatic methylated 6-member ring heterocycles with one or more nitrogen atoms as heteroatom, such as, methylated pyridines, methylated pyrimidines, methylated pyrazines or methylated pyridazines, which exhibit no substituent on the carbon atoms adjacent to the methyl groups to be oxidized. Preferably methylated pyridines, methylated pyrazines and methylated pyrimidines, such as, 2-methylpyridine, 3-methylpyridine, 4-methylpyridine, 2,5-dimethylpyridine, 2,4-dimethylpyridine, 6-chloro-3-methylpyridine, 2-chloro-3-ethyl-6-methylpyridine, 4,6-dimethylpyrimidine, 2-methylpyrazine, 2,5-dimethylysyazine, 2,6-dimethylpyrazine, 2,3,5-trimethylpyrazine and 2-chloro-3,6-dimethylpyrazine, are used.

The compounds, which serve the microorganism as the carbon source and energy source, such as, p-xylene, m-xylene, p-cymene, m-cymene or toluene, also suitably serve for induction of the enzymes of the microorganisms responsible for the reaction. This enzyme induction can also be performed with compounds which do not serve the microorganism as the carbon source and energy source, such as, for example, mono- and di-substituted methyl, ethyl and chlorine toluenes, benzyl alcohols, p-chlorobenzaldehyde, o-xylene and o-cymene, which have already been described as enzyme inducers for the decomposition of aromatic hydrocarbons [Abril M.A. et al., J. Bacteriol., Vol. 171, (1989), pages 6782 to 6789]. These compounds are suitably fed in gaseous form, for example, according to the data of Hosler and Eltz [Microbiol. Conversion of p-Xylene in Stirred Fermenters, *Fermentation Advances,* Acad. Press, Inc. N.Y., (1969), pages 789 to 805]. The compounds used for induction can also be fed in liquid form.

Suitably the inducer is added so that the specific inducer decomposition rate is between 0.01 and 50 mmol/g dry weight/hour.

Preferably the microorganisms are cultivated in a mineral medium with p-xylene until the cell suspension contains 0.01 to 200 g dry weight. Suitably, the microorganisms are cultivated at a pH of 5 to 9, preferably at a pH of 7 to 8. The cultivation is suitably performed in all process steps at a temperature of 15° to 90° C., preferably at 25° to 35° C.

Other cultures, which suitably then have the same composition, can be inoculated with the cultured biomass.

In the process according to the invention the cultured biomass is the starting point for the microbiological oxidation of methyl group in the heterocycles in the so-called biotransformation phase, which can be performed continuously or by batch.

After the biomass cultivation, process step (b) involves stopping the feeding of the inducer.

Process steps (c) to (e) characterize, in the invention process, the so-called biotransformation phase. The culture medium and the culture conditions in the biotransformation phase are largely similar to that of the biomass cultivation.

The biotransformation phase is characterized in that:

Process step (c): then the feedstock, the methylated aromatic 5- or 6-ring heterocycle, and the carbon source and energy source are added to the culture solution until the microorganisms exhibit a decrease of the activity for the biotransformation Process step (d): then the activity of the microorganisms is regenerated by feeding of the inducer, optionally also by simultaneously stopping the feeding of the carbon source and energy source, until the specific inducer decomposition rate is between 0.01 and 50 mmol/g drying weight/hour; and Process step (e): process steps (b) to (d) are repeated so that the biotransformation can be performed over prolonged periods and, thus, the maximal product concentration and/or a continuous production process are attained and high space-time yields are achieved.

The feedstock, the heterocycle, is suitably fed so that the concentration in the culture medium is between 0.0001 and 5 percent, preferably between 0.01 and 1 percent.

The compounds usual among experts and, e.g., known in the literature for Pseudomonas strains can be used as the carbon source and energy source [The Prokaryotes, Ed. by M. P. Starr, H. Stolp, H. G. Trueper, A. Balow and H. G. Schlegel, Springer Verlag, (pages 670 to 679, 1981]. Suitable carbon sources and energy sources are carbohydrates, sugar alcohols, low-boiling aliphatic alcohols, aliphatic fatty acids or amino acids. Preferably glucose and/or glycerol and/or glutamate is used. This carbon source and energy source is suitably fed so that the specific substrate decomposition rate is between 0.01 and 200 mmol/g dry weight/hour.

After cultivation in a biotransformation phase performed in a batch, i.e., generally after 10 to 250 hours, a product concentration in the culture of more than 100 mmol/l can be achieved.

In a modification of the process, after the completion of the fermentation, a part of the culture solution is removed, and with the remaining part, to which new culture medium has been added, a new biotransformation cultivation is started.

With the so-called repeated biotransformation process, the volumetric productivity of the fermentation can be reduced. The volumetric productivity can be increased still more by simultaneously adding new medium and removing the culture solution (continuous process).

A relief of the culture can be achieved by the feedstock (the heterocycle) being desalted and purified by an ion exchanger or by electrodialysis.

Recovery of the products from the culture solution takes place by the usual methods and can be suitably performed continuously or in batch—continuous recovery is preferred. The separation of the biomass can be performed, e.g., by centrifugation, ultrafiltration or microfiltration.

The concentrated product solutions obtained both in electrodialysis and by ion exchanging can be concentrated either by evaporation or by reverse osmosis and then can be azeotropically dehydrated.

If the product is recovered continuously by electrodialysis [e.g., according to Eymondt and Wandrey, Chem. Ing. Tech., vol. 62, No. 2, (1990), pages 134 and 135], the productivity can be increased even more.

Preferably 5-methyl-2-pyrazinecarboxylic acid or 6-methyl-2-pyrazinecarboxylic acid, most especially 5-methyl-2-pyrazinecarboxylic acid, is produced according to the invention process.

EXAMPLE b 1

Production of 5-methyl-2-pyrazinecarboxylic acid

Pseudomonas putida ATCC 33015 was cultivated in a mineral medium [Kulla et al., Arch. Microbiol., 135, (1983), pages 1 to 7] with p-xylene as sole carbon source and energy source in a fermenter at pH 7.0 and a temperature of 30° C. The enzyme inducer p-xylene was fed in gaseous form according to the data of Hosler and Eltz [Microbiol. Conversion of p-Xylene in Stirred Fermenters, *Fermentation Advances*, Acad. Press, Inc., N.Y., (1969), pages 789 to 805] until a biomass concentration of 7.8 g dry weight/l was reached. Then the feeding of the inducer was stopped, and 2,5-dimethylpyrazine and 50 percent glucose solution were added to the fermenter at a rate of 1 g/l/h. After 4 hours, when the biotransformation activity of the biomass had dropped to about 80 percent, p-xylene (2 h) was again added up to a specific inducer decomposition rate of 0.51 mmol/g dry weight/h, with the simultaneous stopping of the addition of glucose. The drop of the biotransformation activity of the biomass was detected by the consumption of the lye that was consumed for neutralization of the product. After that, glucose and p-xylene were alternately added as described until the concentration of 5-methyl-2-pyrazine-carboxylic acid had reached value of 101 mmol/l, which corresponded to a yield of 95 percent, relative to the 2,5-dimethylpyrazine used.

EXAMPLE 2

Production of 6-methyl-2-pyrazinecarboxylic acid

*Pseudomonas putida* ATCC 33015 was cultivated analogously to Example 1 until the biomass concentration of 7.8 g dry weight/l was reached. Then the feeding of the inducer was stopped and 2,6-dimethylpyrazine and 50 percent glucose solution were added to the fermenter at a rate of 1 g/l/h. After 4 hours, when the biotransformation activity of the biomass had dropped to about 75 percent, p-xylene (2 h) was again fed up to a specific inducer decomposition rate of 0.45 mmol/g dry weight/h, and the addition of glucose was stopped. The drop of the biotransformation activity of the biomass was detected by the consumption of the lye that was consumed for neutralization of the product. After that, glucose and p-xylene were alternately added as described until the concentration of 6-methyl-2-pyrazine-carboxylic acid had reached a value of 105 mmol/l, which corresponded to a yield of 95 percent, relative to the 2,6-dimethylpyrazine used.

What is claimed is:

1. Microbiological process for the oxidation of a methyl group on an aromatic 5- or 6-ring heterocycle, and the heterocycle exhibiting no substituent on the carbon atom adjacent to the methyl group to be oxidized to the correpsonding carboxylic acid, comprising: feeding to a culture medium, containing xylene-utilizing microorganisms of the strain *Pseudomonas putida* having the designation ATCC 33015 or an effective nutant thereof:

(i) an inducer which induces enzymes of the microorganisms and which does not serve the microorganisms as carbon source and energy source, (ii) the methylated aromatic 5- or 6-ring heterocycle as substrate for the biotransformation, and optionally (iii) one or more carbon and energy sources; and after the maximal product concentration is achieved, separating the carboxylic acid.

2. The process according to claim 1 wherein at least one compound is used as the inducer, which serves the microorganism as the carbon source and energy source.

3. The process according to claim 2 wherein the inducer is selected from the group consisting of toluene, m-xylene, p-xylene, m-cymene and p-cymene.

4. The process according to claim 1 wherein compounds are used as inducer, which do not serve the microorganism as the carbon source and energy source.

5. The process according to claim 4 wherein the inducer is selected from the group consisting of mono- or di-substituted methyl, ethyl, and chlorine toluenes, benzyl alcohols, p-chlorobenzaldehyde, o-xylene and o-cymene.

6. The process according to claim 2 wherein:
(a) the microorganisms are cultivated with the inducer until enough cells for the production are present;
(b) then feeding of the inducer is stopped;
(c) then the methylated aromatic 5- or 6-ring heterocycle and the carbon source and energy source are added until the microorganisms exhibit a decrease of activity for the biotransformation;
(d) then the activity of the microorganisms is regenerated by feeding of the inducer, optionally by simultaneous stopping of the carbon source and energy source; and
(e) process steps (b) to (d) are repeated so that the biotransformation can be performed over prolonged periods and, thus, the maximal product concentration and/or continuous production process is performed and a high space-time yield is achieved.

7. The process according to claim 6 wherein the inducer is added so that the specific inducer decomposition rate is between 0.01 and 50 mmol/g dry weight/hour.

8. The process according to claim 6 wherein the methylated aromatic 5- or 6- ring heterocycle is added so that the concentration in the culture medium is between 0.0001 and 5 percent.

9. The process according to claim 6 wherein the carbon source and energy source is added so that the specific substrate decomposition rate is between 0.01 and 200 mmol/g dry weight/hour.

10. The process according to claim 6 wherein a carbohydrate, sugar alcohol, low-boiling aliphatic alcohol, aliphatic fatty acid or amino acid is used as the carbon source and energy source.

11. The process according to claim 10 wherein the product is separated continuously or by batch.

12. The process according to claim 1 for the production of 5-methyl-2-pyrizinecarboxylic acid wherein 2,5-dimethylpyrazine is used as the substrate.

13. The process according to claim 1 for the production of 6-methyl-2-pyrazinecarboxylic acid wherein 2,6-dimethylpyrazine is used as the substrate.

14. The process according to claim 1 wherein:
(a) the microorganisms are cultivated with the inducer until enough cells for the production are present;
(b) then feeding of the inducer is stopped;
(c) then the methylated aromatic 5- or 6-ring heterocycle and the carbon source and energy source are added until the microorganisms exhibit a decrease of activity for the biotransformation;
(d) then the activity of the microorganisms is regenerated by feeding of the inducer, optionally by simultaneous stopping of the carbon source and energy source; and
(e) process steps (b) to (d) are repeated so that the biotransformation can be performed over prolonged periods and, thus, the maximal product concentration and/or continuous production process is performed and a high space-time yield is achieved.

15. The process according to claim 11 wherein the inducer is added so that the specific inducer decomposition rate is between 0.01 and 50 mmol/g dry weight/hour.

16. The process according to claim 11 wherein the methylated aromatic 5- or 6-ring heterocycle is added so that the concentration in the culture medium is between 0.0001 and 5 percent.

17. The process according to claim 11 wherein the carbon source and energy source is added so that the specific substrate decomposition rate is between 0.01 and 200 mmol/g dry weight/hour.

18. The process according to claim 11 wherein a carbohydrate, sugar alcohol, low-boiling aliphatic alcohol, aliphatic fatty acid or amino acid is used as the carbon source and energy source.

19. The process according to claim 11 wherein the product is separated continuously or by batch.

* * * * *